US006537307B1

(12) United States Patent
Augustine et al.

(10) Patent No.: US 6,537,307 B1
(45) Date of Patent: *Mar. 25, 2003

(54) REUSABLE THERMAL BLANKET WITH A MULTILAYER SHEET

(75) Inventors: Scott Douglas Augustine, Bloomington; Douglas Arnold Hall; Rudolf Andreas Deibel, both of Eden Prairie, all of MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 175 days.

This patent is subject to a terminal disclaimer.

(21) Appl. No.: 09/652,224

(22) Filed: Aug. 30, 2000

Related U.S. Application Data

(63) Continuation of application No. 09/277,628, filed on Mar. 26, 1999, now Pat. No. 6,168,612.

(51) Int. Cl.$^7$ .................................................. A61F 7/00
(52) U.S. Cl. ...................................................... 607/107
(58) Field of Search ................................ 607/107, 104, 607/96, 114; 601/16, 15; 602/12, 13

(56) References Cited

U.S. PATENT DOCUMENTS

| | | | |
|---|---|---|---|
| 4,572,188 A | | 2/1986 | Augustine et al. .......... 128/380 |
| 4,696,065 A | | 9/1987 | Elenteny |
| 5,265,599 A | * | 11/1993 | Stephenson et al. ........ 607/104 |
| 5,300,101 A | | 4/1994 | Augustine et al. .......... 607/107 |
| 5,300,102 A | | 4/1994 | Augustine et al. .......... 607/107 |
| 5,324,320 A | | 6/1994 | Augustine et al. .......... 607/107 |
| 5,336,250 A | | 8/1994 | Augustine ................... 607/107 |
| 5,350,417 A | | 9/1994 | Augustine ................... 607/104 |
| 5,443,488 A | * | 8/1995 | Namenye et al. ........... 607/104 |
| 5,658,325 A | | 8/1997 | Augustine |
| 5,749,109 A | * | 5/1998 | Kappel ........................... 5/423 |
| 5,800,483 A | * | 9/1998 | Vought ........................ 607/104 |

FOREIGN PATENT DOCUMENTS

| | | |
|---|---|---|
| EP | 0280839 | 9/1988 |
| EP | 0421310 A1 | 4/1991 |
| FR | 2716104 | 8/1995 |
| WO | WO 97/14381 | 4/1997 |

* cited by examiner

*Primary Examiner*—Linda C. M. Dvorak
*Assistant Examiner*—Jocelyn Ram
(74) *Attorney, Agent, or Firm*—Gray Cary Ware & Freidenrich; Terrance A. Meador

(57) ABSTRACT

An inflatable thermal blanket with a multilayer sheet and a method of use are disclosed for delivering thermally-controlled air to a person. The apparatus includes an inflatable structure formed from joining a first sheet and a second sheet. An inlet is provided into the inflatable structure for receiving thermally-controlled air. A multilayer sheet, made from a plurality of sheets releasably attached together, is attached to the second sheet. Means are provided for exhausting the thermally-controlled air from the inflatable thermal blanket. In the method of use, the inflatable thermal blanket is deployed in a first use and a source of thermally-controlled air is attached to the inflation port admitting thermally-controlled air into the inflatable structure and exhausting thermally-controlled air. Additionally, the inflatable thermal blanket may be reused by detaching the lowest layer of the multilayer sheet, exposing another layer of the multilayer sheet and deploying the inflatable thermal blanket in a second or later use. These steps may be repeated until the last layer of the multilayer sheet is used, when the thermal blanket may be discarded. In an alternate embodiment, when the multilayer sheet is exhausted it is detached and another multilayer base sheet is attached to the inflatable structure and the thermal blanket is used again.

39 Claims, 6 Drawing Sheets

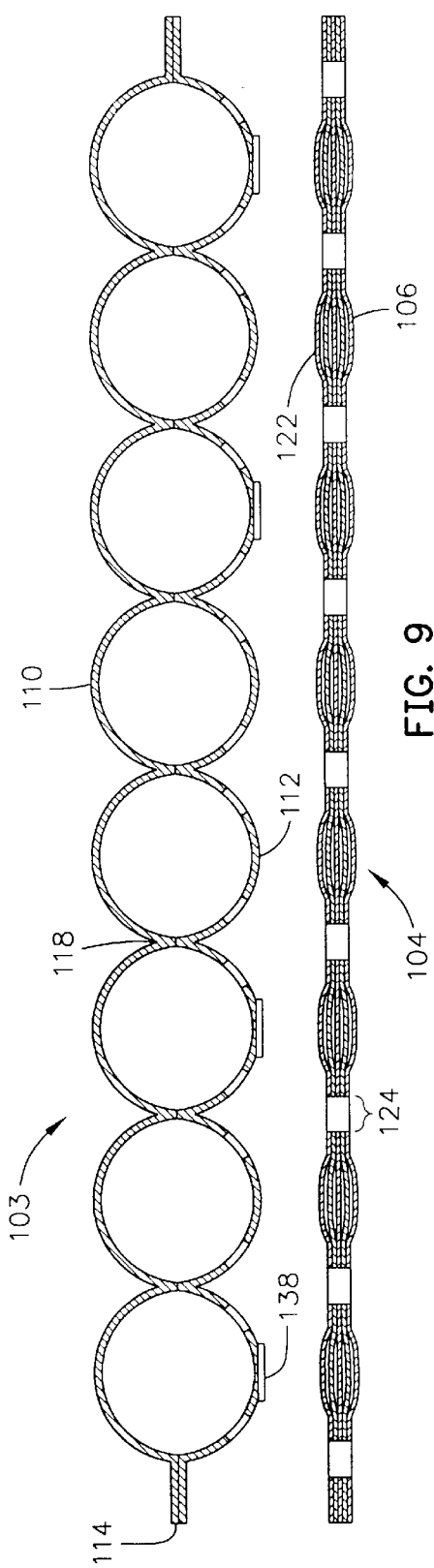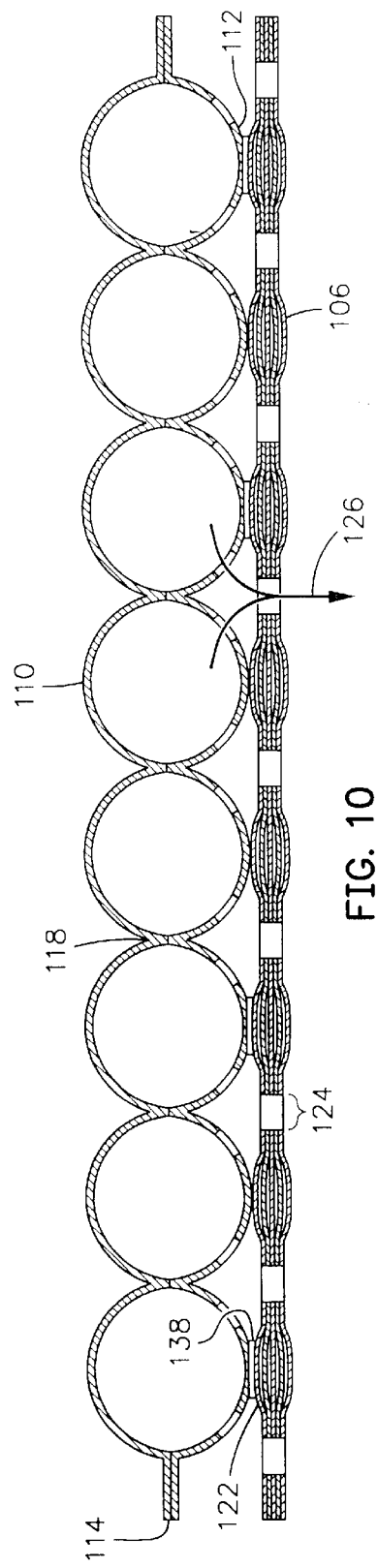

REUSABLE THERMAL BLANKET WITH A MULTILAYER SHEET

This is a continuation of U.S. patent application Ser. No. 09/277,628, filed Mar. 26, 1999 now U.S. Pat. No. 6,168,612.

BACKGROUND OF THE INVENTION

1. Field of the Invention

This invention relates generally to inflatable thermal blankets and, more particularly, to an inflatable thermal blanket with a multilayer sheet in which, after use, a layer of the multilayer sheet can be detached, thereby enabling the inflatable thermal blanket to be reused.

2. Description of the Related Art

It often is necessary to control a person's body temperature using means external to the person. For example, it is important to keep a person warm during surgery and to warm the person post-operatively to reduce the risk of hypothermia. 60–70% of surgical persons will experience hypothermia during surgery, if not treated. Many studies have been published showing the detrimental effects of hypothermia that occur during surgery. Such effects include a higher incidence of infections, more bleeding, more adverse cardiac events, higher death rates, slower recovery and longer hospitalizations. One means of preventing or treating hypothermia is the inflatable thermal blanket.

Inflatable thermal blankets have been in clinical use for the past ten years. Such a blanket may be inflated with cooled or warmed air and deployed over a person in need of thermal management where it bathes the person in a flow of cool or warm air. Persons needing thermal management include accidental hypothermia victims, persons with fever and persons undergoing surgery. Numerous research studies have shown that inflatable thermal blankets provide a highly effective and safe mode of thermal management.

In one use, an inflatable thermal blanket is inflated with warm air and placed adjacent a person. Warm air is expelled through a surface of the device that faces the person, creating a warmed environment about the person, thereby reducing and even reversing the transfer of heat from the person to the environment. Inflatable thermal blankets are provided for generalized and specialized uses, for which various inflatable structures have been developed. See, for example, U.S. Pat. Nos. 4,572,188; 5,300,101; 5,300,102; 5,324,320; 5,336,250 and 5,350,417 assigned to Augustine Medical, Inc. and incorporated herein by this reference. With the introduction of the BAIR HUGGER® family of inflatable thermal blankets by Augustine Medical, Inc., clinicians have been enabled to provide safe and effective thermal therapy to persons in a number of clinical settings, including surgery and recovery.

An inflatable thermal blanket typically includes a surface through which the inflating medium is expelled. Such a surface may include apertures formed in it by a manufacturing process, or may comprise an air-permeable material, for example. The blanket is deployed with the surface facing the person and the thermally-controlled air which inflates the device is exhausted from the blanket, through the surface, toward the person. The temperature of the thermally controlled air can be precisely controlled in order to warm or cool a person.

The majority of inflatable thermal blankets sold today are disposable "single use" products made of polymeric films and non-woven material. Extreme pressure to control costs has forced many health care providers to carefully examine their use of such disposables. In some cases, providers may reuse "single use" blankets which have been in contact with a previous person's skin and bodily fluids. There is no suitable way to clean and sterilize these "single use" blankets and therefore this practice can transmit infection from one person to another.

In response to the trend toward reuse of medical products, some manufacturers are now providing inflatable thermal blankets made of durable materials which can be cleaned and sterilized between uses. These blankets also appeal to the providers who believe that disposables are not friendly to the environment. However, reusable inflatable thermal blankets also have several draw-backs. First, they are expensive. Second, their durability is severely limited by the high temperatures and strong detergents necessary to clean and sterilize them. Finally, the detergents themselves are environmentally unfriendly.

From the discussion above, it should be apparent that there is a need for an inflatable thermal blanket that can be safely and economically used multiple times on one or more persons without requiring sterilization between uses. The present invention satisfies this need.

SUMMARY OF THE INVENTION

Broadly, the present invention concerns an inflatable thermal blanket with a multilayer sheet providing a surface through which air is transferred from the blanket toward a person. Presently, once an inflatable thermal blanket has been used on a person, this surface may be contaminated. Consequently, the blanket must be cleaned and sterilized or discarded. The advantage of a multilayer sheet is that the layers in the plurality of layers that make up the multilayer sheet may be detached from the sheet one or more at a time and discarded. So, following use of the inflatable thermal blanket, the contaminated layer or layers may be removed to render the inflatable thermal blanket ready for use again.

In an example that embodies, but which does not limit, the invention, an inflatable thermal blanket with a multilayer base sheet comprises an inflatable structure formed by attaching a first sheet to a second sheet. An inflation port is provided in the inflatable structure for admitting a stream of thermally-controlled air (e.g., heated or cooled air) into the inflatable structure. The multilayer sheet is assembled from a plurality bf sheets releasably attached together. The multilayer sheet is attached to the second sheet of the inflatable structure. Finally, a plurality of air passageways through the second sheet and the multilayer sheet allow the thermally-controlled air to flow through the inflatable structure. In a preferred embodiment, one or more layers of the multilayer sheet can be removed at one time without detaching the rest of the plurality of sheets. In this way, contaminated sheets can be removed individually, or multiply, and the inflatable thermal blanket can be reused.

Other features and advantages of the present invention should be apparent from the following description of the preferred embodiments, which illustrate, by way of example, the principles of the invention.

BRIEF DESCRIPTION OF THE DRAWING

The nature, objects, and advantages of the invention will become more apparent to those skilled in the art after considering the following detailed description in connection with the accompanying drawings, in which like reference numerals designate like parts throughout, wherein:

FIG. 9 and FIG. 10 are cross-sectional views of FIG. 3 showing another embodiment of the inflatable structure.

DESCRIPTION OF THE PREFERRED EMBODIMENTS

The figures show an inflatable thermal blanket in an inflated condition for clarity and ease of understanding. It is to be understood however, that the invention applies to inflatable thermal blankets in an uninflated condition as well.

The invention concerns a unitary, integral structure with a plurality of layers that may be detached one-by-one from the unitary integral structure. The structure is referred to as a "multilayer sheet". As the following discussion will reveal, each layer of the multilayer is best embodied as a sheet. However, in order to avoid confusing each sheet of a layer with the multilayer sheet, the individual sheets of the multilayer sheet will be referred to in the description and claims as "layers", with the understanding that "layer" may mean "sheet".

Figure 1:
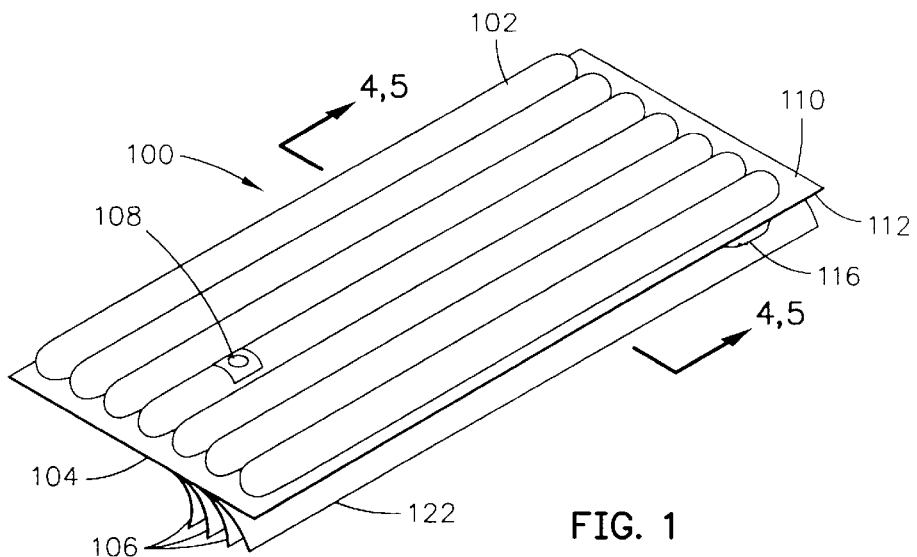
FIG. 1 is a perspective view showing one embodiment of the present invention of an inflatable thermal blanket with a multilayer sheet disposed on a base sheet.

FIG. 1 is an instructive illustration of the present invention, in the form of an inflatable thermal blanket 100. The inflatable thermal blanket 100 includes an inflatable structure 102 and a multilayer sheet 104. The multilayer sheet 104 is made from a plurality of sheets or layers 106 assembled together in such a manner as to make each layer detachable from a neighboring layer. The inflatable thermal blanket 100 also includes an inflation port 108 located in the inflatable structure 102, which may be connected to a tube (not shown) leading to an external heater/blower unit (not shown). Together, the tube and blower unit provide pressurized thermally-controlled air (for either heating or cooling) to inflate the thermal blanket 100.

Figure 2:
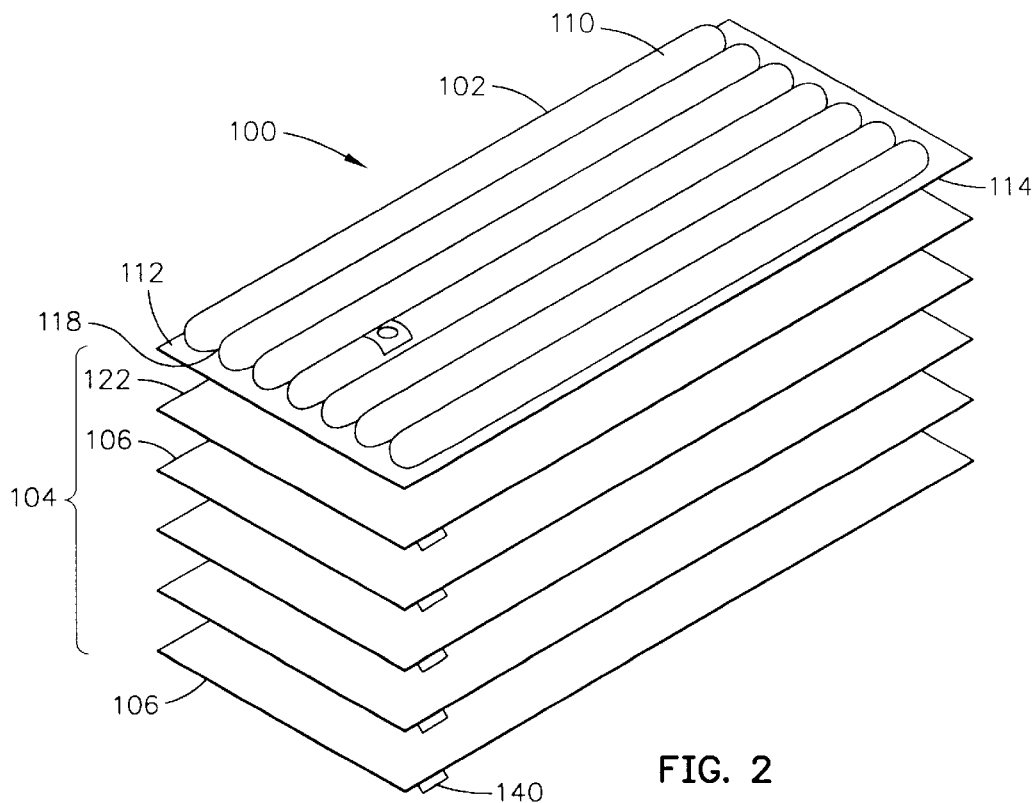
FIG. 2 is an exploded view of FIG. 1 showing the inflatable structure and the multiple layers of the sheet.
Figure 3:
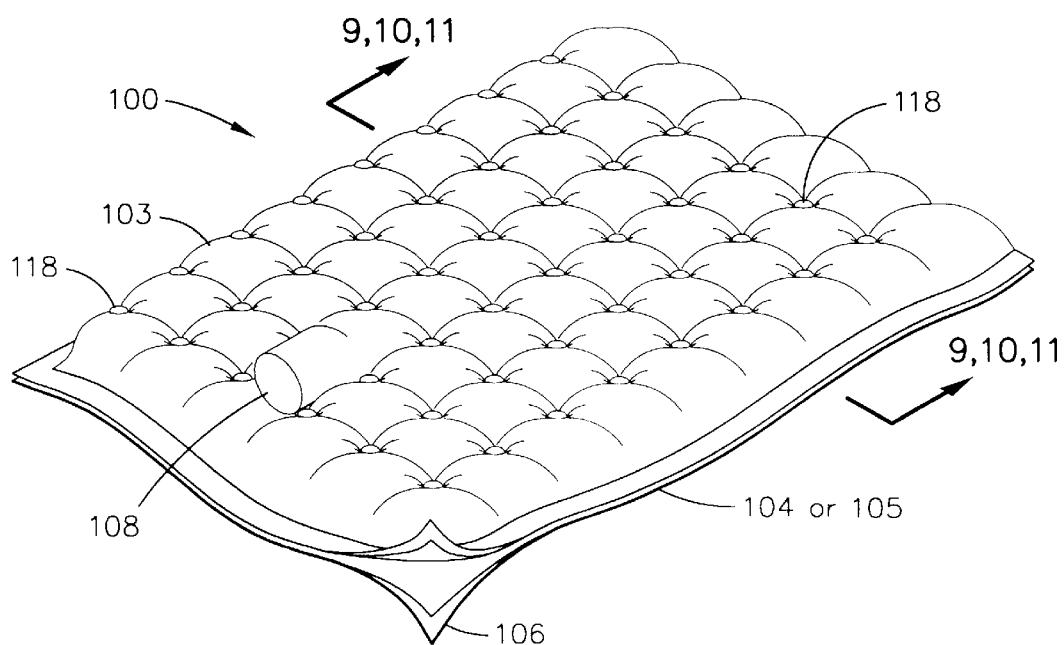
FIG. 3 is a perspective view similar to FIG. 1 showing another embodiment of the inflatable structure.

FIG. 2 is an exploded view of FIG. 1 showing the inflatable structure 102 and the multilayer sheet 104. The inflatable structure 102 of the thermal blanket 100 includes a first sheet 110 and a second sheet 112 (see also FIGS. 4 and 5). The sheet 110 is preferably made of a polymeric film material. The second sheet 112 may be made of a polymeric film, a fibrous or non-woven material or a combination of these materials. The first sheet 110 and second sheet 112 are joined at one or more locations to form the inflatable structure 102. For example, the sheets may be joined along a substantially continuous seam near the peripheries of the sheets, but other configurations are possible. The location of such a seam with reference to the first sheet 110 is indicated by reference numeral 114. The first sheet 110 and second sheet 112 may also be joined together at one or more locations 118 within the peripheral seam at 114. These additional locations 118 help to direct the air flow and prevent the inflatable structure 102 from blowing up like a beach ball. FIG. 3 illustrates another inflatable structure 103. The inflatable structure 103 is similar to inflatable structure 102 but the locations 118 are a plurality of stake points, forming a quilt-like structure. These embodiments are but two examples of some of the shapes and structures that the inflatable thermal blanket can be formed into. Many other, but nevertheless equivalent variations are possible.

Referring again to FIG. 2, the inflatable thermal blanket 100 includes one or more additional layers 106 that are joined together to form the multilayer sheet 104. The additional layers 106 include a layer 122, which is adjacent to the second sheet 112 (i.e., the layer closest to the inflatable structure). Preferably, the additional layers 106 are made of a non-woven material that is hydrophobic and therefore fluid repelling or a non-woven material that has been "waterproofed" by laminating it to a polymeric film layer. Alternately, the additional layers 106 may be made of a polymeric film, fibrous materials, woven or non-woven materials or a combination of these materials.

For the inflatable thermal blanket 100 to heat or cool a person, it must be attached to a unit that provides a stream of warmed or cooled air. The inflation port 108 allows the temperature controlled stream of air to enter the inflatable structure 102, the usual connection being an air hose. At least one surface of the thermal blanket 100, the air is released through a plurality of air passageways, which allow the air to flow from the thermal blanket 100 toward a person (not shown).

Figure 4:
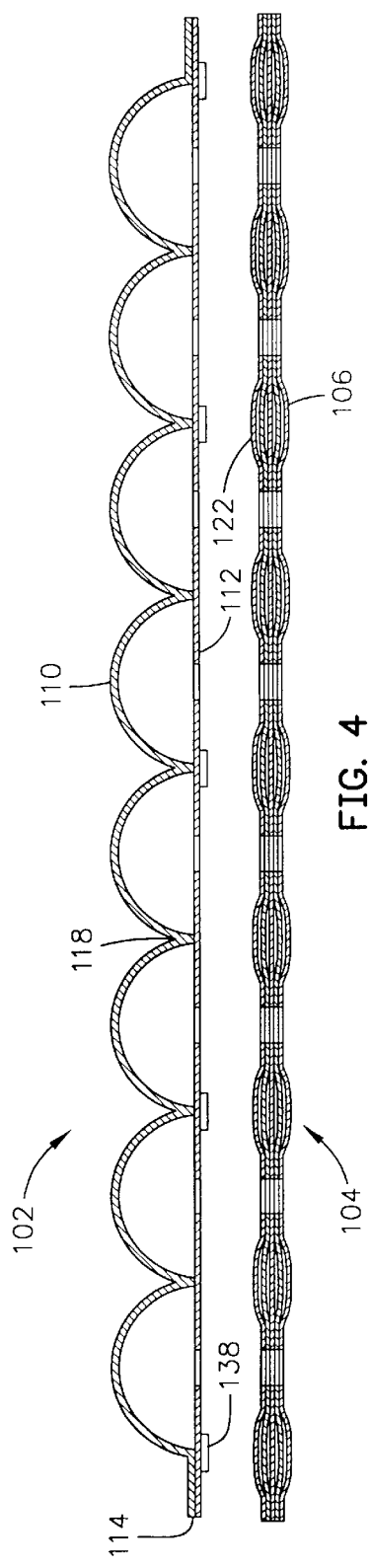
FIG. 4 is a cross-sectional view of FIG. 1 prior to the attachment of the multiple layers to the inflatable structure.

FIG. 4 shows a cross-sectional view of the inflatable structure 102 when inflated, with the multilayer sheet 104 unattached. The inflatable structure 102 is assembled with the first sheet 110 and the second sheet 112 joined together along a substantially continuous seam at 114. As is evident, when the structure 102 is inflated it manifests parallel flattened tubes. Also shown is the multilayer sheet 104 assembled with the plurality of layers 106, one of which may be designated as a "closest" layer 122. It is contemplated by the inventors that the closest layer 122 of the multilayer sheet 104 could also serve as the second sheet 112 by directly attaching the first sheet 110 to the closest layer 122.

Figure 5:
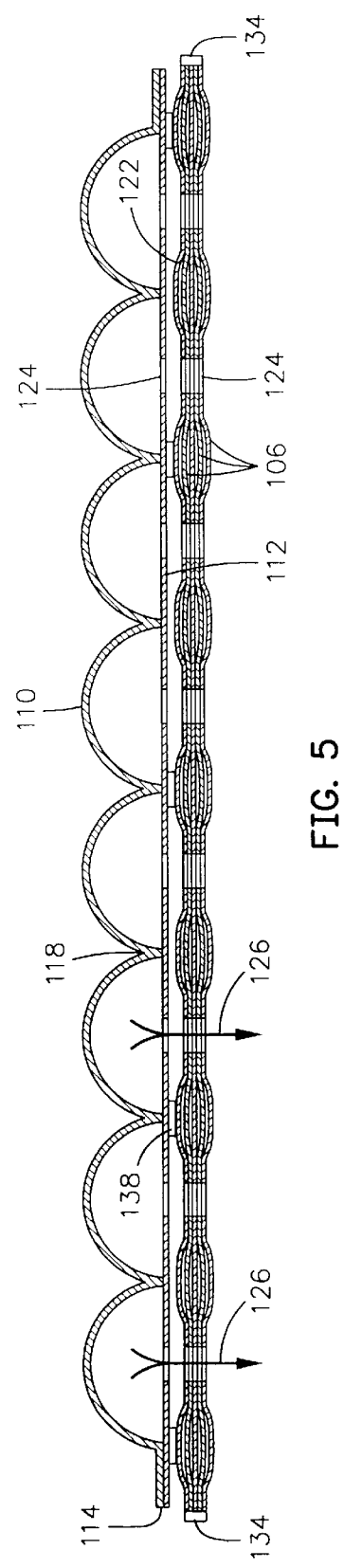
FIG. 5 is a cross-sectional view of FIG. 1 showing the attachment of the multiple layers to the inflatable structure.

FIG. 5 is a cross-sectional view of the thermal blanket 100 showing the inflatable structure 102 assembled with the multilayer sheet 104. As discussed above, pressurized air flows out of the thermal blanket 100 through the second sheet 112. In the second sheet 112, a plurality of air passageways 124 are formed to allow air to flow from the inflatable structure 102. In addition to these air passageways there are also air passageways 124 through the multilayer sheet 104. Preferably these air passageways 124 are created through all of the layers 106 by forming the air passageways 124 through all of the layers 106 of the sheet 104 at once. Alternately, the air passageways 124 may be inherent if the layers 106 are made of a non-woven or woven material (i.e., a porous material). Finally, air passageways 124 may be formed in the individual layers 106 before stacking.

Figure 6:
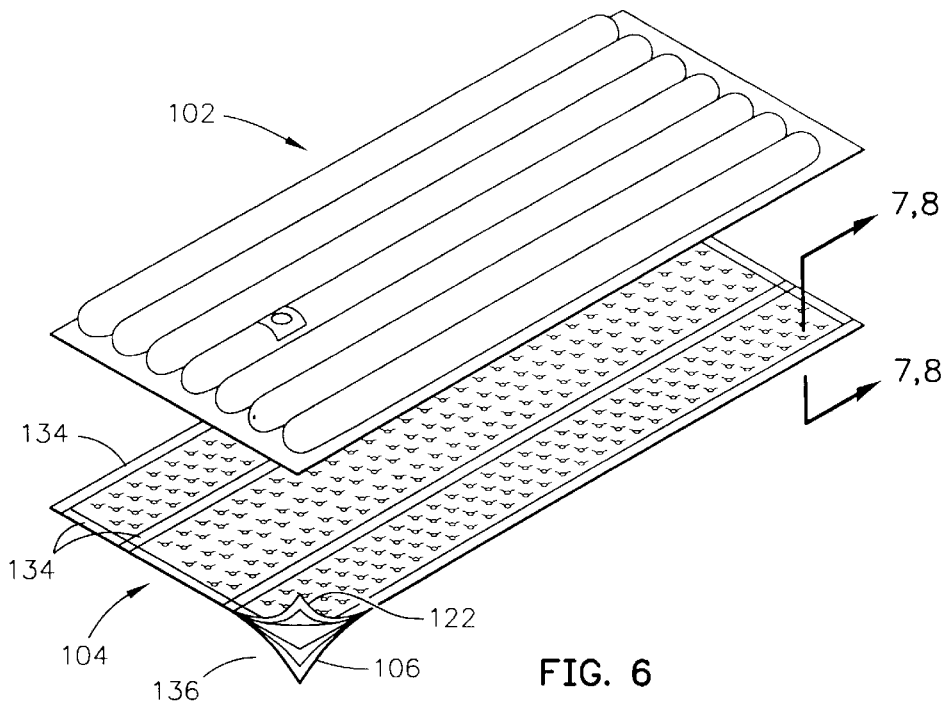
FIG. 6 is another exploded view of FIG. 1 showing the multiple layers laminated before attachment to the inflatable structure.

FIG. 6 is an exploded view similar to FIG. 2 showing the layers 106 assembled into the multilayer sheet 104. In one embodiment, the layers 106 are joined together at 134. However, the layers are separated at a corner 136 to allow the separation of an individual layer 106 when required (described in more detail below).

Figure 7:
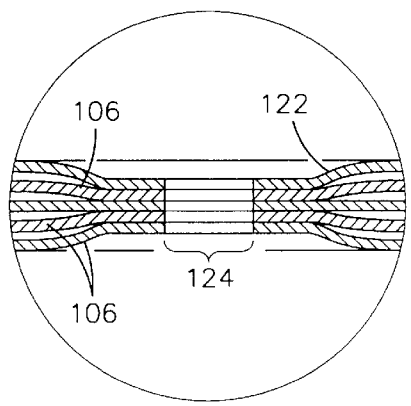
FIG. 7 is a sectional view 7—7 of FIG. 6 showing one embodiment of the multiple layers with a melted hole.
Figure 8:
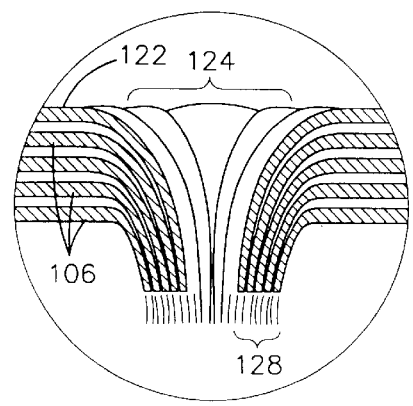
FIG. 8 is a sectional view 8—8 of FIG. 6 showing another assembly embodiment of the multiple layers with a punched hole.

FIGS. 7 and 8 show alternate methods of forming the air passageways 124 in the multilayer sheet 104. In the preferred embodiment, the air passageways 124 may be formed by melting and/or by punching in such a manner as to join the layers 106 together at the perimeter of each hole. If a passageway is created by melting for example, as shown in FIG. 7, the melted material joins each layer 106 to the next at the passageway, forming the multilayer sheet 104. If the passageway 124 is created by punching, as shown in FIG. 8, the design of the punch and die can be optimized so as to entangle fibers from the adjacent layers 106 of material, resulting in a mechanical "bond" 128 between the layers 106 forming the multilayer sheet 104. Further, a combination of punching and melting may be utilized. The advantage of this design is that the bonds joining the layers 106 at the perimeters of the passageways 124 assure that the corresponding passageways 124 in each layer 106 are oriented with one another. Precisely aligning the passageways 124 in the layers 106 reduces the total resistance to air flow by providing a direct air flow path 126 through all of the layers 106. This direct air flow path 126 is advantageous because it provides more air flow through the inflatable thermal blanket. Alternately, if the layers 106 are "breathable" (i.e., formed of porous material) and do not require holes punched in them for air flow, the layers 106 may be joined (adhesively or thermally, for example) together at multiple locations 130 across their surfaces or at their peripheries or at combinations of these locations (see FIG. 11).

Referring again to FIGS. 4 and 5, when attaching the multilayer sheet 104 to the inflatable structure 102, the "closest" layer 122 is placed proximate the second sheet 112 and attached at multiple locations 138. For example, the closest layer 122 may be adhesively attached at 138 to the second sheet 112. Alternately, the closest layer 122 may be thermally bonded at 138 to the second sheet 112. In another embodiment, the closest layer 122 is removeably attached to the second sheet 112 at 138 with a hook-and-eye material. Preferably the closest layer 122 is attached to the second sheet 112 at multiple locations 138 across its surface.

Finally, since the inflatable thermal blanket with a multilayer sheet is reusable in multiple successive deployments, each layer 106 must be detachable from an adjacent layer 106. In the preferred embodiment, the bottom-most layer 106 (i.e., the layer 106 furthest from layer 122) can be separated (i.e., detached) from the adjacent layer by tearing the relatively weak thermal and/or entangled fiber bond 128 at the periphery of each passageway 124. This allows the bottom-most layer of the thermal blanket 100, which was in contact with a person in a first deployment and therefore may have been contaminated, to be discarded after use. The remaining thermal blanket 100 is fully functional and clean for the next deployment. The closest layer 122 may also be detachable from the second sheet 112. In that way, once all the layers 106 of the multilayer sheet 104 have been used, layer 122 is detached from the second sheet 112 and another multilayer base sheet 104 can be attached and the inflatable thermal blanket can be used in the same manner as previously described.

Optionally, for user convenience and cleanliness, a corner of the multilayer sheet 104 can have the individual layers 106 accessible for the clinician or user to remove, one layer at a time. Optionally, a pull-tab 140 may be attached to each layer 106 for additional ease of use (see FIG. 2). The pull-tab 140 aids the clinician in removing only the bottom-most layer, leaving the remaining blanket 100 intact.

FIGS. 9 and 10 illustrate a possible alternate embodiment of the inflatable structure 103 of FIGS. 3, 4 and 5 with the multilayer sheet 104. As may be appreciated with inspection of these figures, the first and second sheets are joined in such a way as to form parallel fully rounded tubes when the structure 103 is inflated.

Figure 11:
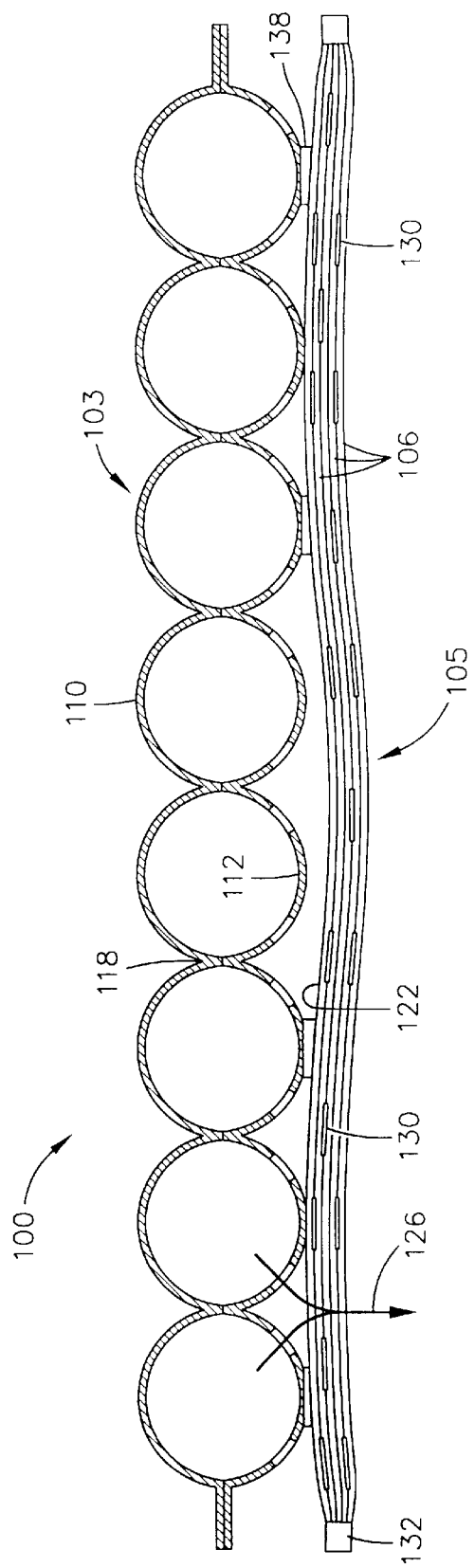
FIG. 11 is a cross-sectional view similar to FIG. 10 showing an alternate structure for the multiple layers.

FIG. 11 shows an alternate embodiment inflatable structure 103 along with an alternate embodiment of the multilayer sheet 105. In this embodiment, the plurality of layers 106 are constructed from a porous or "breathable" material which allows the air to flow from the inflatable structure through the layers of "breathable" material and onto the person. In this construction, the multilayer sheet 105 is constructed from a plurality of layers 106 attached together at a plurality of locations 130. The multilayer sheet 105 may be attached to inflatable structure 103 by adhesive, heat bond or hook-and-eye material as described previously. The layers 106 may also be joined together around the periphery 132.

In one manufacturing embodiment, the layers 106 may be bonded together to form the multilayer sheet 104. In the preferred embodiment, the multilayer sheet 104 is assembled before joining the closest layer 122 to the second sheet layer 112. The preferred material for the layers 106 is a non-woven polyester or polypropylene which has been laminated with a layer of polypropylene or polyethylene film. Unwinding multiple rolls of this material simultaneously, two or more sheets of this material are layered onto one another in a web-type process. The layers 106 are joined together and the passageways 124 are punched through the layers before the individual multilayer sheets are cut from the web. Preferably the passageways 124 are melted and/or punched through all of the layers at once, simultaneously creating passageways 124 and the bonds between the layers 106 at the edge of the holes (as described previously). The passageways 124 may be melted by piercing the layers with a many small hot spikes. Alternately the passageways 124 may be created by melting the material with a laser, jets of hot air or other suitable means.

The layers 106 may be joined using a male plain or serrated punch, cutting onto an anvil material or into a female die. The punches serve two purposes. First they create the passageways 124 through the plural layers 106. Second, the serrations serve to entangle the fibers of the materials 128 of the layers 106, at the periphery of the passageways 124 (see FIG. 8). This creates a mechanical "bond" between the layers and serves to align the passageways 124 in the layers 106. The shape and size of the punches and the serrations may be varied to achieve various levels of bonding. Finally, the punches, anvil or die may be heated to partially or completely melt the material at the periphery of the hole. In this case, the level of heat may be adjusted to control the strength of the bonding between the layers.

Preferably, the layers 106 are bonded together into the multilayer sheet 104 and the air passageways 124 are created before the closest layer 122 is bonded to the second sheet 112 of the previously assembled inflatable structure 102. The closest layer 122 and the second sheet 112 are adhesively bonded together at multiple locations 138 across their surfaces. The adhesive bond may or may not be detachable between the closest layer 122 and the second sheet 112. Alternately this bond 138 may be created by thermally melting the materials of the adjacent layers. Finally, both the inflatable structure 102 and the multilayer sheet 104 are cut from the web simultaneously forming the thermal blanket 100.

For cost and environmental reasons, the thin material of the bottom layer minimizes the amount of material being discarded thereby making a practical, safe, effective, economical and environmentally friendly multiple use forced air thermal blanket.

The description and illustrations thus far have placed a single multilayer sheet on the bottom surface of an inflatable thermal blanket. This is not intended to, and should not, so limit the practice of the invention. As those skilled in the art will appreciate, air may be expelled through surfaces other than the bottom surface of an inflatable thermal blanket. For example, in certain tubular structures, air is expelled through a side surface, or through a side portion of a generally cylindrical surface. In other, pad-like, structures, air may be expelled through a top surface. Moreover, air may be expelled through more than one surface. A multilayer sheet, or a plurality of multilayer sheets according to this invention, may be attached to one or more such surfaces of an inflatable thermal blanket.

While the invention herein disclosed has been described by means of specific embodiments and applications thereof, numerous modifications and variations could be made thereto by those skilled in the art without departing from the scope of the invention set forth in the claims.

We claim:

1. A thermal blanket, comprising:
    an inflatable structure;
    a surface on the inflatable structure;
    an inflation port opening into the inflatable structure;
    a plurality of layers releasably attached together into a multilayer sheet attached to the surface; and
    means for exhausting air through the surface and the multilayer sheet.

2. The thermal blanket of claim 1, wherein the means include a plurality of air passageways.

3. The thermal blanket of claim 2, wherein the air passageways are a plurality of holes punched through the surface and the plurality of layers.

4. The thermal blanket of claim 3, wherein the holes punched through the plurality of layers attach the plurality of layers together to form the multilayer sheet.

5. The thermal blanket of claim 2, wherein the air passageways include a plurality of holes melted through the plurality of layers.

6. The thermal blanket of claim 5, wherein the holes melted through the plurality of layers join the layers together to form the multilayer sheet.

7. The thermal blanket of claim 1 wherein the means include the plurality of layers being made from a porous material.

8. The thermal blanket of claim 1, wherein the plurality of layers are made from a material selected from the group consisting of polymeric film material, non-woven fibrous material, woven fibrous material and a combination of polymeric film and non-woven fibrous or woven fibrous materials.

9. The thermal blanket of claim 1 further comprising:
    the inflatable structure including a first sheet joined to a second sheet at a plurality of locations to form a plurality of interconnected inflation structures.

10. The thermal blanket of claim 9, wherein the surface is a surface of the second sheet and the second sheet is made of a different material than the plurality of layers.

11. The thermal blanket of claim 9, wherein the surface is a surface of the second sheet and the second sheet is made of the same material as the first sheet.

12. The thermal blanket of claim 1, wherein the plurality of layers are releasably attached to each other such that when one layer is removed, the remaining layers stay attached together.

13. The thermal blanket of claim 12, wherein each of the plurality of layers is releasably attached to an adjacent layer at a plurality of locations.

14. The thermal blanket of claim 1, wherein a plurality of holes are punched through the plurality of layers mechanically attaching them together.

15. The thermal blanket of claim 1, wherein a plurality of holes are melted through the plurality of layers attaching them together.

16. A reusable thermal blanket for delivering thermally-controlled air to a person, comprising:
    a first sheet and a second sheet joined together to form an inflatable structure with a surface;
    an inflation port opening into the inflatable structure;
    a multilayer sheet releasably attached to the surface; and
    a plurality of air passageways through the surface and the multilayer sheet for exhausting the thermally-controlled air.

17. The reusable thermal blanket of claim 16, wherein the multilayer sheet is constructed from a plurality of sheets releasably attached to each other.

18. The reusable thermal blanket of claim 16, wherein the air passageways through the surface are not aligned with the air passageways in the multilayer sheet.

19. The thermal blanket of claim 16, wherein the air passageways through the surface are aligned with the air passageways in the multilayer sheet.

20. The reusable thermal blanket of claim 16 further comprising:
    the second sheet being joined to the first sheet at a plurality of locations, forming a plurality of interconnected structures.

21. The reusable thermal blanket of claim 16, wherein the multilayer sheet includes a plurality of layers that are made from a material selected from the group consisting of polymeric film material, non-woven fibrous material, woven fibrous material and a combination of polymeric film and non-woven fibrous or woven fibrous materials.

22. The reusable thermal blanket of claim 16, wherein the multilayer sheet is removably attached to the surface with hook-and-eye material.

23. A method of making a reusable thermal blanket with a multilayer sheet, the method comprising the steps of:
    joining a first sheet to a second sheet to form an inflatable structure with a surface;
    providing an inflation port opening into the inflatable structure;
    forming a multilayer sheet by releasably attaching together a plurality of sheets;
    attaching the multilayer sheet to the surface; and
    providing a plurality of air passageways in each of the surface and the multilayer sheet.

24. The method as defined in claim 23, wherein the step of providing a plurality of air passageways further includes the step of melting holes with heated rods.

25. The method as defined in claim 23, wherein the step of providing a plurality of air passageways further includes the step of melting holes with laser beams.

26. The method as defined in claim 23, wherein the step of providing a plurality of air passageways further includes the step of melting holes with jets of heated air.

27. The method as defined in claim 23, wherein the step of providing a plurality of air passageways further includes the step of piercing holes with spikes.

28. The method as defined in claim 23, wherein the step of providing a plurality of air passageways further includes the step of punching holes with a die.

29. The method as defined in claim 23, wherein the plurality of air passageways are provided through a non-woven fibrous material.

30. The method as defined in claim 23, wherein the plurality of air passageways are provided through a woven fibrous material.

31. The method as defined in claim 23, wherein the plurality of sheets are thermally bonded together.

32. The method as defined in claim 23, wherein the plurality of sheets are thermally and mechanically bonded together.

33. The method as defined in claim 23, wherein the plurality of sheets are adhesively bonded together.

34. The method as defined in claim 23, wherein the step of attaching includes adhesively bonding the multilayer sheet to the surface at a plurality of locations.

35. The method as defined in claim 23, wherein the step of attaching includes thermally bonding the multilayer sheet to the surface at a plurality of locations.

36. A method of delivering thermally-controlled air with a reusable thermal blanket having multilayer sheet, the method comprising the steps of:

providing a reusable thermal blanket comprising:
    a first sheet and a second sheet joined together to form an inflatable structure with a surface;
    an inflation port opening Into the inflatable structure;
    a multilayer sheet attached to the surface, the multilayer sheet being made from a plurality of releasably attached sheets; and
    a plurality of air passageways through each of the surface and the multilayer base sheet;

placing the reusable thermal blanket in a first deployment;

attaching a source of thermally-controlled air to the inflation port;

admitting thermally-controlled air into the Inflatable structure; and exhausting thermally-controlled air through the plurality of air passageways.

37. The method as defined in claim 36, further comprising the steps of:

detaching a sheet from the multilayer sheet;

placing the inflatable thermal blanket in a second deployment; and exhausting thermally-controlled air through the plurality of air passageways.

38. The method defined in claim 37, further comprising the step of:

repeating the steps in claim 37 for a plurality of deployments.

39. A reusable thermal blanket for delivering thermal-controlled air to a person, comprising:

a sheet;

a plurality of layers releasably attached together into a multilayer sheet attached to the sheet to form an inflatable structure;

an inflation port opening into the inflatable structure; and means for exhausting the thermally-controlled air through the multilayer sheet.

* * * * *